(12) United States Patent
Lecuivre et al.

(10) Patent No.: US 11,471,256 B2
(45) Date of Patent: Oct. 18, 2022

(54) PROSTHESIS FOR INGUINAL HERNIA

(71) Applicant: Sofradim Production, Trévoux (FR)

(72) Inventors: Julie Lecuivre, Jassans-Riottier (FR); Xavier Bourges, Saint Etienne sur Chalaronne (FR)

(73) Assignee: SOFRADIM PRODUCTION, Trevoux (FR)

( * ) Notice: Subject to any disclaimer, the term of this patent is extended or adjusted under 35 U.S.C. 154(b) by 364 days.

(21) Appl. No.: 16/128,549

(22) Filed: Sep. 12, 2018

(65) Prior Publication Data
US 2019/0008625 A1  Jan. 10, 2019

Related U.S. Application Data

(62) Division of application No. 14/366,332, filed as application No. PCT/EP2012/076983 on Dec. 27, 2012, now Pat. No. 10,080,639.

(30) Foreign Application Priority Data

Dec. 29, 2011 (FR) ..................................... 11/62531

(51) Int. Cl.
*A61F 2/00* (2006.01)
*D04B 21/12* (2006.01)
*A61L 27/34* (2006.01)

(52) U.S. Cl.
CPC ............ *A61F 2/0063* (2013.01); *A61L 27/34* (2013.01); *D04B 21/12* (2013.01);
(Continued)

(58) Field of Classification Search
CPC ............. B05D 1/00; A61F 2/0063; A61F 2/00
See application file for complete search history.

(56) References Cited

U.S. PATENT DOCUMENTS

| 1,187,158 | A | 6/1916 | Mcginley |
| 3,054,406 | A | 9/1962 | Usher |

(Continued)

FOREIGN PATENT DOCUMENTS

| CA | 1317836 C | 5/1993 |
| CN | 201879864 U | 6/2011 |

(Continued)

OTHER PUBLICATIONS

Canadian Office Action issued in corresponding Canadian application No. 2,858,003 dated May 3, 2019, 3 pages.

(Continued)

*Primary Examiner* — Cachet I Proctor
(74) *Attorney, Agent, or Firm* — Weber Rosselli & Cannon LLP

(57) ABSTRACT

The present invention relates to a prosthesis (1) for the repair of an inguinal hernia, which prosthesis (1) is intended to be implanted by a posterior or open laparoscopic route and comprises: an openworked textile (2) made of biocompatible material, comprising a first face (2a) intended to be placed facing the biological tissues of the inguinal region, and a second face (2b) arranged opposite said first face and intended to be placed facing the peritoneum, said first face being provided with fastening means that are able to fix said textile in said biological tissues of the inguinal region, characterized in that at least a part of said second face (2b) is covered with a non-porous coating (7) composed of a material that is hydrosoluble at 37° C. and non-hydrosoluble at 25° C. The invention also relates to a method for producing such a prosthesis.

17 Claims, 6 Drawing Sheets

(52) U.S. Cl.
CPC ............... *A61F 2002/0068* (2013.01); *A61F 2230/0063* (2013.01); *A61F 2250/003* (2013.01); *A61F 2250/0008* (2013.01); *D10B 2403/0112* (2013.01); *D10B 2501/0632* (2013.01); *D10B 2509/08* (2013.01)

(56) References Cited

U.S. PATENT DOCUMENTS

| | | |
|---|---|---|
| 3,118,294 A | 1/1964 | Van Laethem |
| 3,122,479 A | 2/1964 | Smith |
| 3,124,136 A | 3/1964 | Usher |
| 3,272,204 A | 9/1966 | Artandi et al. |
| 3,276,448 A | 10/1966 | Kronenthal |
| 3,320,649 A | 5/1967 | Naimer |
| 3,364,200 A | 1/1968 | Ashton et al. |
| 3,570,482 A | 3/1971 | Shigeru et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Melton et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,563,184 A | 1/1986 | Korol |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,728,642 A | 3/1988 | Pawelchak et al. |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | Mcmurray |
| 5,350,583 A | 9/1994 | Yoshizato et al. |
| 5,356,432 A | 10/1994 | Rutkow et al. |
| 5,368,549 A | 11/1994 | Mcvicker |
| 5,368,602 A | 11/1994 | Torre |
| 5,370,650 A | 12/1994 | Jonathan et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | Mcgregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |

(56) References Cited

U.S. PATENT DOCUMENTS

| | | | |
|---|---|---|---|
| 5,910,149 A | 6/1999 | Kuzmak | |
| 5,911,731 A | 6/1999 | Pham et al. | |
| 5,916,225 A | 6/1999 | Kugel | |
| 5,919,232 A | 7/1999 | Chaffringeon et al. | |
| 5,919,233 A | 7/1999 | Knopf et al. | |
| 5,922,026 A | 7/1999 | Chin | |
| 5,931,165 A | 8/1999 | Reich et al. | |
| 5,942,278 A | 8/1999 | Hagedorn et al. | |
| 5,962,136 A | 10/1999 | Dewez et al. | |
| 5,972,022 A | 10/1999 | Huxel | |
| RE36,370 E | 11/1999 | Li | |
| 5,993,844 A | 11/1999 | Abraham et al. | |
| 5,994,325 A | 11/1999 | Roufa et al. | |
| 5,997,895 A | 12/1999 | Narotam et al. | |
| 6,001,895 A | 12/1999 | Harvey et al. | |
| 6,008,292 A | 12/1999 | Lee et al. | |
| 6,015,844 A | 1/2000 | Harvey et al. | |
| 6,039,686 A | 3/2000 | Robert | |
| 6,042,534 A | 3/2000 | Gellman et al. | |
| 6,042,592 A | 3/2000 | Schmitt | |
| 6,043,089 A | 3/2000 | Sugiyama et al. | |
| 6,051,425 A | 4/2000 | Morota et al. | |
| 6,056,688 A | 5/2000 | Benderev et al. | |
| 6,056,970 A | 5/2000 | Greenawalt et al. | |
| 6,057,148 A | 5/2000 | Sugiyama et al. | |
| 6,063,396 A | 5/2000 | Kelleher | |
| 6,066,776 A | 5/2000 | Goodwin et al. | |
| 6,066,777 A * | 5/2000 | Benchetrit | A61F 2/0063 424/423 |
| 6,071,292 A | 6/2000 | Makower et al. | |
| 6,077,281 A | 6/2000 | Das | |
| 6,080,194 A | 6/2000 | Pachence et al. | |
| 6,083,522 A | 7/2000 | Chu et al. | |
| 6,090,116 A | 7/2000 | D Aversa et al. | |
| 6,113,623 A | 9/2000 | Sgro | |
| 6,120,539 A | 9/2000 | Eldridge et al. | |
| 6,132,765 A | 10/2000 | Dicosmo et al. | |
| 6,143,037 A | 11/2000 | Goldstein et al. | |
| 6,153,292 A | 11/2000 | Bell et al. | |
| 6,162,962 A | 12/2000 | Hinsch et al. | |
| 6,165,488 A | 12/2000 | Tardy et al. | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,179,872 B1 | 1/2001 | Bell et al. | |
| 6,180,848 B1 | 1/2001 | Flament et al. | |
| 6,191,334 B1 | 2/2001 | Patterson | |
| 6,197,325 B1 | 3/2001 | Macphee et al. | |
| 6,197,934 B1 | 3/2001 | Devore et al. | |
| 6,197,935 B1 | 3/2001 | Doillon et al. | |
| 6,210,439 B1 | 4/2001 | Firmin et al. | |
| 6,214,020 B1 | 4/2001 | Mulhauser et al. | |
| 6,221,109 B1 | 4/2001 | Geistlich et al. | |
| 6,224,616 B1 | 5/2001 | Kugel | |
| 6,241,768 B1 | 6/2001 | Agarwal et al. | |
| 6,258,124 B1 | 7/2001 | Darois et al. | |
| 6,262,332 B1 | 7/2001 | Ketharanathan | |
| 6,264,702 B1 | 7/2001 | Ory et al. | |
| 6,267,772 B1 | 7/2001 | Mulhauser et al. | |
| 6,270,530 B1 | 8/2001 | Eldridge et al. | |
| 6,277,397 B1 | 8/2001 | Shimizu | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,306,079 B1 | 10/2001 | Trabucco | |
| 6,306,424 B1 | 10/2001 | Vyakarnam et al. | |
| 6,312,474 B1 | 11/2001 | Francis et al. | |
| 6,319,264 B1 | 11/2001 | Tormala et al. | |
| 6,328,686 B1 | 12/2001 | Robert | |
| 6,334,872 B1 | 1/2002 | Termin et al. | |
| 6,337,389 B1 * | 1/2002 | Wolfinbarger, Jr. | A61L 27/24 530/356 |
| 6,383,201 B1 | 5/2002 | Dong | |
| 6,391,060 B1 | 5/2002 | Ory et al. | |
| 6,391,333 B1 | 5/2002 | Li et al. | |
| 6,391,939 B2 | 5/2002 | Tayot et al. | |
| 6,408,656 B1 | 6/2002 | Ory et al. | |
| 6,410,044 B1 | 6/2002 | Chudzik et al. | |
| 6,413,742 B1 | 7/2002 | Olsen et al. | |
| 6,425,924 B1 | 7/2002 | Rousseau | |
| 6,428,978 B1 | 8/2002 | Olsen et al. | |
| 6,436,030 B2 | 8/2002 | Rehil | |
| 6,440,167 B2 | 8/2002 | Shimizu | |
| 6,443,964 B1 | 9/2002 | Ory et al. | |
| 6,447,551 B1 | 9/2002 | Goldmann | |
| 6,447,802 B2 | 9/2002 | Sessions et al. | |
| 6,448,378 B2 | 9/2002 | Devore et al. | |
| 6,451,032 B1 | 9/2002 | Ory et al. | |
| 6,451,301 B1 | 9/2002 | Sessions et al. | |
| 6,454,787 B1 | 9/2002 | Maddalo et al. | |
| 6,477,865 B1 | 11/2002 | Matsumoto | |
| 6,479,072 B1 | 11/2002 | Morgan et al. | |
| 6,485,503 B2 | 11/2002 | Jacobs et al. | |
| 6,500,464 B2 | 12/2002 | Ceres et al. | |
| 6,500,777 B1 | 12/2002 | Wiseman et al. | |
| 6,509,031 B1 | 1/2003 | Miller et al. | |
| 6,511,958 B1 | 1/2003 | Atkinson et al. | |
| 6,514,286 B1 | 2/2003 | Leatherbury et al. | |
| 6,514,514 B1 | 2/2003 | Atkinson et al. | |
| 6,540,773 B2 | 4/2003 | Dong | |
| 6,541,023 B1 | 4/2003 | Andre et al. | |
| 6,548,077 B1 | 4/2003 | Gunasekaran | |
| 6,554,855 B1 | 4/2003 | Dong | |
| 6,559,119 B1 | 5/2003 | Burgess et al. | |
| 6,566,345 B2 | 5/2003 | Miller et al. | |
| 6,575,988 B2 | 6/2003 | Rousseau | |
| 6,576,019 B1 | 6/2003 | Atala | |
| 6,596,002 B2 | 7/2003 | Therin et al. | |
| 6,596,304 B1 * | 7/2003 | Bayon | A61L 15/325 424/444 |
| 6,599,323 B2 | 7/2003 | Melican et al. | |
| 6,599,524 B2 | 7/2003 | Li et al. | |
| 6,599,690 B1 | 7/2003 | Abraham et al. | |
| 6,610,006 B1 | 8/2003 | Amid et al. | |
| 6,613,348 B1 | 9/2003 | Jain | |
| 6,616,685 B2 | 9/2003 | Rousseau | |
| 6,623,963 B1 | 9/2003 | Mueller et al. | |
| 6,627,215 B1 | 9/2003 | Dale et al. | |
| 6,630,414 B1 | 10/2003 | Matsumoto | |
| 6,637,437 B1 | 10/2003 | Hungerford et al. | |
| 6,638,284 B1 | 10/2003 | Rousseau et al. | |
| 6,645,226 B1 | 11/2003 | Jacobs et al. | |
| 6,652,594 B2 | 11/2003 | Francis et al. | |
| 6,652,595 B1 | 11/2003 | Nicolo | |
| 6,653,450 B1 | 11/2003 | Berg et al. | |
| 6,656,206 B2 | 12/2003 | Corcoran et al. | |
| 6,660,280 B1 | 12/2003 | Allard et al. | |
| 6,669,735 B1 | 12/2003 | Pelissier | |
| 6,670,018 B2 | 12/2003 | Fujita et al. | |
| 6,682,760 B2 | 1/2004 | Noff et al. | |
| 6,685,714 B2 | 2/2004 | Rousseau | |
| 6,706,684 B1 | 3/2004 | Bayon et al. | |
| 6,706,690 B2 | 3/2004 | Reich et al. | |
| 6,712,859 B2 | 3/2004 | Rousseau et al. | |
| 6,719,795 B1 | 4/2004 | Bryan et al. | |
| 6,723,335 B1 | 4/2004 | Moehlenbruck et al. | |
| 6,726,660 B2 | 4/2004 | Hessel et al. | |
| 6,730,299 B1 | 5/2004 | Tayot et al. | |
| 6,736,823 B2 | 5/2004 | Darois et al. | |
| 6,736,854 B2 | 5/2004 | Vadurro et al. | |
| 6,737,371 B1 | 5/2004 | Planck et al. | |
| 6,743,435 B2 | 6/2004 | Devore et al. | |
| 6,746,458 B1 | 6/2004 | Cloud | |
| 6,752,834 B2 | 6/2004 | Geistlich et al. | |
| 6,755,868 B2 | 6/2004 | Rousseau | |
| 6,773,723 B1 | 8/2004 | Spiro et al. | |
| 6,783,554 B2 | 8/2004 | Amara et al. | |
| 6,790,213 B2 | 9/2004 | Cherok et al. | |
| 6,790,454 B1 | 9/2004 | Abdul et al. | |
| 6,800,082 B2 | 10/2004 | Rousseau | |
| 6,833,408 B2 | 12/2004 | Sehl et al. | |
| 6,835,336 B2 | 12/2004 | Watt | |
| 6,852,330 B2 | 2/2005 | Bowman et al. | |
| 6,869,938 B1 | 3/2005 | Schwartz et al. | |

(56) References Cited

U.S. PATENT DOCUMENTS

| | | |
|---|---|---|
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III et al. |
| 7,682,381 B2 | 3/2010 | Rakos et al. |
| 7,709,017 B2 | 5/2010 | Tayot et al. |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 2001/0008930 A1* | 7/2001 | Tayot .................. A61L 31/041 527/200 |
| 2002/0087174 A1 | 7/2002 | Capello |
| 2002/0095218 A1 | 7/2002 | Carr et al. |
| 2002/0132240 A1* | 9/2002 | Ashkenazi ............. C07K 14/47 435/6.17 |
| 2003/0086975 A1 | 5/2003 | Ringeisen |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0062910 A1 | 4/2004 | Morrison |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | Mcalexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0243149 A1* | 10/2008 | Kockerling ........... A61F 2/0063 606/151 |
| 2008/0255593 A1 | 10/2008 | St-Germain |
| 2009/0005867 A1 | 1/2009 | Lefranc et al. |
| 2009/0035341 A1 | 2/2009 | Wagener et al. |
| 2009/0036996 A1 | 2/2009 | Roeber |
| 2009/0036997 A1* | 2/2009 | Bayon .................. A61L 27/56 623/23.75 |
| 2009/0068250 A1 | 3/2009 | Gravagna et al. |
| 2009/0105526 A1 | 4/2009 | Piroli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0192532 A1* | 7/2009 | Spinnler ............... A61F 2/0063 606/153 |
| 2009/0204129 A1 | 8/2009 | Fronio |

(56) References Cited

U.S. PATENT DOCUMENTS

| | | |
|---|---|---|
| 2009/0216338 A1 | 8/2009 | Gingras et al. |
| 2009/0240288 A1* | 9/2009 | Guetty .................. A61F 2/0063 606/285 |
| 2009/0270999 A1 | 10/2009 | Brown |
| 2009/0281558 A1 | 11/2009 | Li et al. |
| 2009/0318752 A1* | 12/2009 | Evans ................ A61B 17/0482 600/37 |
| 2010/0104608 A1 | 4/2010 | Abuzaina et al. |
| 2010/0318108 A1 | 12/2010 | Datta et al. |
| 2011/0015760 A1 | 1/2011 | Kullas |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet et al. |
| 2011/0257666 A1* | 10/2011 | Ladet ..................... A61L 27/48 606/151 |
| 2011/0320009 A1* | 12/2011 | Ladet ..................... A61L 27/48 623/23.72 |
| 2012/0010636 A1* | 1/2012 | Boey ..................... A61L 27/34 606/151 |
| 2012/0010637 A1* | 1/2012 | Stopek .................. A61F 2/0063 606/151 |
| 2012/0016388 A1 | 1/2012 | Houard et al. |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell et al. |
| 2012/0179176 A1 | 7/2012 | Wilson et al. |
| 2012/0197415 A1 | 8/2012 | Montanari et al. |
| 2013/0078285 A1* | 3/2013 | Ladet ..................... A61L 27/58 424/400 |
| 2014/0044861 A1 | 2/2014 | Boey et al. |
| 2014/0364684 A1 | 12/2014 | Lecuivre et al. |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 0544485 A1 | 6/1993 |
| EP | 0552576 A1 | 7/1993 |
| EP | 0611561 A1 | 8/1994 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 0827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 0898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1216717 A1 | 6/2002 |
| EP | 1216718 A1 | 6/2002 |
| EP | 0693523 B1 | 11/2002 |
| EP | 1273312 A2 | 1/2003 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2724563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2846548 A1 | 5/2004 |
| FR | 2859624 A1 | 3/2005 |
| FR | 2863277 A1 | 6/2005 |
| FR | 2876020 A1 | 4/2006 |
| FR | 2884706 A1 | 10/2006 |
| FR | 2929834 A1 | 10/2009 |
| FR | 2953709 A1 | 6/2011 |
| GB | 1174814 A | 12/1969 |
| GB | 2051153 A | 1/1981 |
| GB | 2306110 A | 4/1997 |
| JP | H0332677 A | 2/1991 |
| JP | H05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9310731 A1 | 6/1993 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 0181667 A1 | 11/2001 |
| WO | 0207648 A1 | 1/2002 |
| WO | 0217853 A2 | 3/2002 |
| WO | 02078568 A1 | 10/2002 |
| WO | 03002168 A1 | 1/2003 |

(56) References Cited

FOREIGN PATENT DOCUMENTS

| WO | 2004004600 A1 | 1/2004 | |
|---|---|---|---|
| WO | 2004071349 A2 | 8/2004 | |
| WO | 2004078120 A2 | 9/2004 | |
| WO | 2004103212 A1 | 12/2004 | |
| WO | 2005011280 A1 | 2/2005 | |
| WO | 2005013863 A2 | 2/2005 | |
| WO | 2005018698 A1 | 3/2005 | |
| WO | 2005048708 A1 | 6/2005 | |
| WO | 2005105172 A1 | 11/2005 | |
| WO | 2006018552 A1 | 2/2006 | |
| WO | 2006023444 A2 | 3/2006 | |
| WO | 2007048099 A2 | 4/2007 | |
| WO | 2009031035 A2 | 3/2009 | |
| WO | 2009071998 A2 | 6/2009 | |
| WO | 2010043978 A2 | 4/2010 | |
| WO | 2011007062 A1 | 1/2011 | |
| WO | 2011026987 A1 | 3/2011 | |
| WO | WO-2011026987 A1 * | 3/2011 | ............ A61L 27/54 |
| WO | 2011038740 A1 | 4/2011 | |
| WO | 2011042811 A2 | 4/2011 | |

OTHER PUBLICATIONS

Amid, R., "Lichtenstein tension-free hernioplasty: Its inception, evolution, and principles," Hernia, 2004; pp. 1-7, 8, published online Sep. 2003.
Australian Examination Report dated Dec. 16, 2016 in corresponding Australian Patent Application No. 2012360857, 3 pages.
Blondin, C. et al., "Inhibition of Complement Activation by Natural Sulfated Polysaccharides (Fucans) from Brown Seaweed," Molecular Immuol., Mar. 1994, pp. 247-253, 31(4).
Blondin, C. et al., "Relationships between chemical characteristics and anticomplementary activity of fucans," Biomaterials, Mar. 1996, pp. 597-603, 17(6).
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Canadian Office Action issued in corresponding Canadian application No. 2,858,003 dated Oct. 12, 2018, 3 pages.
Dhastan, "Tension Free Open Inguinal Hernia Repair Using an Innovative Self Gripping Semi-Resorbable Mesh," J. Min. Access. Surg., Sep. 2006, pp. 139-143, vol. 2.
Chen, G. et al., "A Hybrid Network of Synthetic Polymer Mesh and Collagen Sponge," The Royal Society of Chemistry 2000, Chem. Commun., Jul. 2000, pp. 1505-1506.
Chinese Office Action dated Apr. 5, 2016 in corresponding Chinese Patent Application No. 201280065573.1, together with English language translation, 23 pages.
Chinese Office Action dated Oct. 21, 2016 in corresponding Chinese Patent Application No. 201280065573.1 together with English translation, 22 pages.
Chinese Office Action, Application No. 2012800655731 dated Jul. 28, 2015 and English translation.
Collins, R. et al., "Use of collagen film as a dural substitute: Preliminary animal studies," Journal of Biomedical aterials Research, Feb. 1991, pp. 267-276, vol. 25.
Covidien, "Parietex ProGrip Self-Fixating Mesh," Hernia Repair Products, retrieved Dec. 7, 2012, http://www.covidien.com/campaigns/pagebuilder.aspx?topiciD=172431 &page=Hernia:Parietex>, pp. 1-2.
Covidien, "Procedures Parietex ProGrip Self-Fixating Mesh," Hernia Solutions, retrieved Dec. 7, 2012, (select United States), pp. 1-2.
Dixit et al., "Oral Strip Technology: Overview and Future Potential," Journal of Controlled Release, Jun. 2009, pp. 34-107, vol. 139.
Dr. S. Raz, "The Karl Mayer Guide to Tehnical Textiles," Jan. 2000, pp. 1-36, Obertshausen, Germany.

Ellouali, M. et al., "Antitumor Activity of Low Molecular Weight Fucans Extracted from Brown Seaweed Ascophyllum nodosum," Anticancer Res , Nov.-Dec. 1993, pp. 2011-2020, 12 (6A).
European Office Action dated Dec. 19, 2017 in corresponding European Patent Application No. 12812670.3, 3 pages.
Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Haroun-Bouhedja, F. et al., "Relationship between sulfate groups and biological activities of fucans," Thrombosis Res., Dec. 2000, pp. 453-459, 100(5).
Hirano, S. et al., "The blood biocompatibility of chitosan and N-acylchitosans," J. Biomed. Mater. Res., Apr. 1985, 413-417, 19.
International Search Report for PCT/EP12/076983 date of completion is Mar. 11, 2013 (3 pages).
Junge, K. et al., "Functional and Morphologic Properties of a Modified Mesh for Inguinal Hernia Repair," World J. Surg., Sep. 2002, pp. 1472-1480, 26.
Kanabar, V. et al., "Some structural determinants of the antiproliferative effect of heparin-like molecules on human airway smooth muscle," Br. J. Pharmacol., Oct. 2005, pp. 370-777, 146(3).
Klinge, U. et al., "Foreign Body Reaction to Meshes Used for the Repair of Abdominal Wall Hernias," Eur J. Surg, Sep. 1999, pp. 665-673, 165.
Klinge, U. et al., "Functional and Morphological Evaluation of a Low-Weight, Monofilament Polypropylene Mesh for Hernia Repair," J Biomed. Mater. Res., Jan. 2002, pp. 129-136, 63.
Langenbech, M. R. et al., "Comparison of biomaterials in the early postoperative period," Surg Endosc., May 2003, pp. 1105-1109, 17 (7).
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Malette, W. G. et al., "Chitosan, A New Hemostatic," Ann Th. Surg., Jul. 1983, pp. 55-58, 36.
Muzzarelli, R. et al., "Reconstruction of parodontal tissue with chitosan," Biomaterials, Nov. 1989, pp. 598-604, 10.
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Prokop, A. et al., "Water Soluble Polymers for Immunoisolation I: Complex Coacevation and Cytotoxicity," Advances in Polymer Science, Jul. 1998, pp. 1-51, 136.
Rao, B. et al., "Use of chitosan as a biomaterial: Studies on its safety and hemostatic potential," J. Biomed. Mater. Res., Jan. 1997, pp. 21-28, 34.
Rosen, M. et al., "Laparoscopic component separation in the single-stage treatment of infected abdominal wall prosthetic removal," Hernia, 2007, pp. 435-440, 11, published online Jul. 2007.
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220, 18(2).
Strand, S. et al., "Screening of Chitosans and Conditions for Bacterial Flocculation," Biomacromolecules, Mar. 2001, 126-133, 2.
Varum, K. et al., "In vitro degradation rates of partially N-acetylated chitosans in human serum," Carbohydrate Research, Mar. 1997, pp. 99-101, 299.
Welty, G. et al., "Functional impairment and complaints following incisional hernia repair with different polypropylene meshes," Hernia, Aug. 2001; pp. 142-147, 5.
Zyagintseva, T. et al., "Inhibition of complement activation by water-soluble polysaccharides of some far-eastern brown seaweeds," Comparative Biochem and Physiol, Jul. 2000, pp. 209-215, 126(3).

(56) References Cited

OTHER PUBLICATIONS

Communication pursuant to Article 94(3) EPC issued in European Application No. 12812670.3 dated Jul. 28, 2020, 5 pages.

* cited by examiner

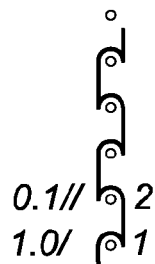 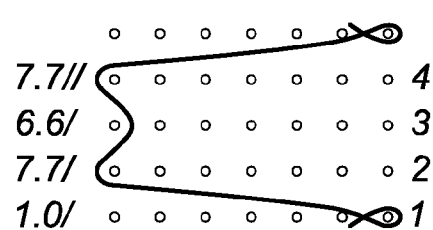 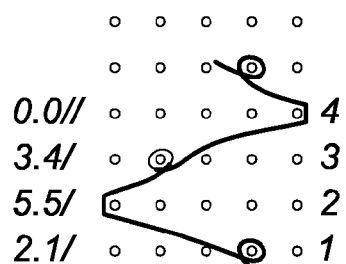
Fig. 8A  Fig. 8B  Fig. 8C
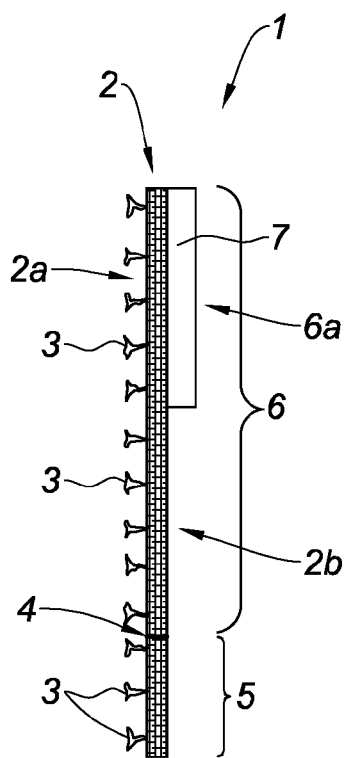 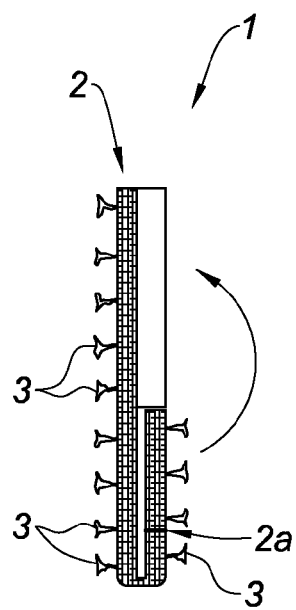 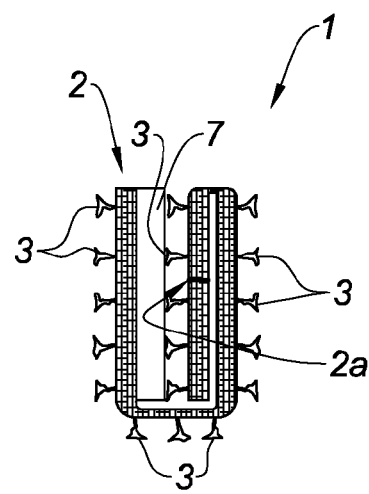
Fig. 9A  Fig. 9B  Fig. 9C

PROSTHESIS FOR INGUINAL HERNIA

This application is a divisional of U.S. Patent Application Ser. No. 14/366,332 filed Jun. 18, 2014, now U.S. Pat. No. 10,080,639, which is a National Stage Application of PCT/EP2012/076983 under 35USC § 371 (a), which claims priority of French Patent Application Serial No. 11/62531 filed Dec. 29, 2011, the disclosures of each of the above-identified applications are hereby incorporated by reference in their entirety.

BACKGROUND

The present invention relates to a prosthesis for the repair of hernias, and in particular a prosthesis adapted for the repair of inguinal hernias by laparoscopy.

In a general manner, prostheses for the repair of the inguinal region and for the treatment of hernias comprise an openworked prosthetic textile which is made of biocompatible synthetic material and may or may not be absorbable, depending on whether the prosthesis is intended to remain permanently in the body of the patient or, by contrast, is intended to disappear once cell recolonization has taken place.

When repair of a hernia in the inguinal region is performed by a posterior and extraperitoneal laparoscopic route, it is important to be able to locate, and to cover with the prosthesis, certain anatomical elements of the anterior wall of the abdomen, which elements may be described as follows, from the inside outwards, and for the right-hand side of the body with reference to FIG. 1:

- to the inside, the anterior retro-parietal space is limited towards the front by the rectus abdominis muscles 16, towards the rear by the peritoneum (not shown), and underneath by the upper margin of the os pubis 17;
- the middle part is limited towards the front by the fascia transversalis (not shown), and the conjoint tendon, with the iliac vessels 11 below, and with the transverse muscle 18 above;
- in the outer part, towards the front there is the internal orifice 19 of the inguinal canal with the elements of the spermatic cord (spermatic vessels and ductus deferens), with the psoas muscle 12 below, and with the transverse muscle 18 above.

The peritoneum is not shown in FIG. 1: it is situated between FIG. 1 and the person looking at FIG. 1. An inguinal hernia is a swelling of the groin caused when a portion of the peritoneum, possibly containing abdominal viscera, passes through the orifice 19 of the inguinal canal. It is necessary to protect this orifice 19 and to push the peritoneum, and possibly the abdominal viscera, back in the direction of the abdominal cavity, and place a barrier, namely a prosthesis, between the peritoneum and the orifice 19 of the inguinal canal.

It will be noted in FIG. 1 that the elements described above are not all in the same spatial plane, but instead are arranged in an oblique arrangement from the top downwards and from the outside inwards. In the case of an inguinal hernia, the prosthesis implanted after reduction of the hernia must ensure satisfactory covering by adapting to the contours of the region and by respecting the obliqueness of the inguinal space, if possible without leaving any empty spaces.

When operating using a posterior and extra-peritoneal route, whether by open surgery or by laparoscopy, the surgeon has to bring the prosthesis into this inguinal region and then place it correctly with respect to all the elements described above.

Furthermore, in order to shorten the duration of an intervention and thereby minimize the number of steps to be performed during an operation, it is possible to use prostheses made from an arrangement of yarns, a knit, a woven or non-woven fabric, comprising barbs protruding outwards from one face of the prosthesis: these barbs constitute structures such as hooks that are able to fix themselves directly in the biological tissues, for example the elements of the inguinal region that have been described above. With such prostheses, it is possible to dispense with steps involving fixing by sutures or staples.

The laparoscopic route requires only very small incisions for the passage of a trocar, through which the prosthesis is delivered to the implantation site. Open surgery is thus avoided, and the patient is soon able to leave hospital. The laparoscopic route is particularly prized in surgical interventions performed in the region of the abdomen, for example in the treatment of hernias.

However, the trocars used in the laparoscopic approach generally have a relatively small calibrated diameter, which can vary from 5 to 15 mm for example, in order to reduce as much as possible the size of the incision that is made. The prosthesis therefore has to be delivered through a conduit of small diameter, and it then has to be deployed at the implantation site.

To perform this step, the prosthesis is generally rolled up on itself, so as to slide it into the conduit of the trocar, or introduced directly with force. However, when the prosthetic textile forming the prosthesis comprises barbs on one face, it can happen that these barbs catch in the body of the textile, thus making subsequent deployment of the prosthesis at the implantation site more difficult. Moreover, because of the obliqueness of the inguinal region and the restricted deployment space, it can prove complicated to deploy the prosthesis and then orient it suitably with respect to the orifice of the inguinal canal.

Therefore, there is still a need for a prosthesis for repair of inguinal hernias that is capable of being delivered through a conduit, such as that of a trocar, to the inguinal region and that is then capable of deploying completely, and preferably easily, and of being oriented and positioned easily once the implantation site in the patient's body has been reached.

The present invention aims to meet such a need.

SUMMARY

A first aspect of the invention is a prosthesis for repair of an inguinal hernia, which prosthesis is intended to be implanted by a posterior or open laparoscopic route and comprises:

an openworked textile made of biocompatible material, comprising a first face intended to be placed facing the biological tissues of the inguinal region, and a second face arranged opposite said first face and intended to be placed facing the peritoneum, said first face being provided with fastening means that are able to fix said textile in said biological tissues of the inguinal region, characterized in that at least a part of said second face is covered with a non-porous coating consisting in a material that is hydrosoluble at 37° C. and non-hydrosoluble at a temperature of less than or equal to 25° C.

The present application also relates to a method for producing a prosthesis of the above type, characterized in that it comprises the following steps:

an openworked textile of biocompatible material is made available comprising a first face, provided with fastening means that are able to fix said textile in biological tissues of the inguinal region, and a second face, at least a part of said second face is covered with a non-porous coating consisting in a material that is hydrosoluble at 37° C. and non-hydrosoluble at 25° C.

In the present application, "biological tissues of the inguinal region" are understood as the biological tissues of the organs or elements of the inguinal region that are shown in FIG. 1 and that are intended to be protected from the peritoneum with a view to repairing the hernia, and in particular the anterior muscle wall, the upper part of the os pubis and of Cooper's ligament, the iliac and spermatic vessels, and part of the psoas muscle.

According to the present application, "textile" is understood as any arrangement or assembly of biocompatible yarns, fibres, filaments and/or multifilaments, for example obtained by knitting, weaving, braiding, or non-woven. The arrangement of yarns of the textile according to the invention defines at least two opposite faces, namely a first face and a second face.

In the present application, "openworked textile" is understood as any textile in which the arrangement of yarns from which it is made defines openings, cells or holes within the thickness of the textile and on the faces of the textile, these openings, cells or holes being able to form channels opening out on each side of the textile. Such an openworked textile permits better tissue integration.

The textile according to the invention additionally comprises fastening means that are able to fix said textile in said biological tissues of the inguinal region. For example, these fastening means are barbs protruding from said first face. These fastening means or barbs can protrude from said first face in a manner substantially perpendicular to the plane of said face or, alternatively, in one or more planes inclined with respect to the plane of said face. These barbs are intended to function as fixing means by anchoring themselves in the biological tissues of the inguinal region.

The textile of the prosthesis according to the invention is covered at least partially on its second face, that is to say on its face opposite the face comprising the barbs, with a non-porous coating composed of a material that is hydrosoluble at 37° C. and non-hydrosoluble at 25° C.

In the present application, "hydrosoluble" is understood as the ability of a material to dissolve in an aqueous composition such as water or in the biological fluids at a given temperature. The hydrosoluble material of the coating of the prosthesis according to the invention has the ability to be hydrosoluble at 37° C. and thus able to dissolve in the biological fluids of a human body, but to be non-hydrosoluble at a temperature of less than or equal to 25° C. and therefore unable to dissolve in an aqueous composition between 20° C. and 25° C.

The time it takes to dissolve at 37° C., for example in the human body, is short, for example varying from 15 minutes to about 4 weeks.

The prosthesis according to the invention can be delivered easily to the implantation site, namely the inguinal region, by means of a trocar and can then be easily deployed at the implantation site. Indeed, the particular nature of the non-porous coating of the second face of the textile of the prosthesis according to the invention makes it possible both to hydrate the prosthesis before its introduction into the trocar and also to fold it optimally in order to facilitate its passage through the trocar and also its subsequent deployment. Indeed, the non-hydrosoluble nature of the non-porous coating at 25° C. makes it possible to hydrate the prosthesis at ambient temperature, that is to say at a temperature ranging from 20 to 25° C., without compromising the integrity of said coating. It has been found that, with prior hydration of this kind, the textile, and therefore the prosthesis, could be made more pliable and therefore easier to manipulate so as to fold it optimally for easy passage through the trocar and for optimized deployment on leaving the trocar. Thus, once it has been hydrated, it is possible for the prosthesis according to the invention to be folded such that most of the fastening means find themselves in contact with said non-porous coating, which has not yet dissolved. Thus, the fastening means of the first face of the textile do not in practice catch in the openings of the second face of the same textile, even when the prosthesis is pushed through the trocar, in which it is subject to the stress exerted by the inner walls of the trocar.

Thus, when the prosthesis leaves the trocar and arrives in the inguinal region, the fastening means are not entangled in the textile, and the prosthesis according to the invention can be easily deployed. At the implantation site in the human body, where the temperature is about 37.5° C., the non-porous coating dissolves upon contact with the aqueous biological fluids. Therefore, this avoids an excessive amount of foreign material being introduced long-term into the patient.

In one embodiment of the invention, said non-porous coating is present over the whole of the second face of said textile. It thus suffices to roll up the textile of the prosthesis according to the invention on itself, for example with the fastening means to the outside, in order to form a roll of the prosthesis that can be introduced into and then pushed through a trocar. Since the fastening means are thus in contact with the non-porous coating, they do not become entangled in the openings of the textile, and the deployment of the prosthesis when it leaves the trocar is easy.

In one embodiment of the prosthesis according to the invention, with said textile having the overall shape of a rectangle with length L and width l, said textile determines in the direction of its width l a first part called the upper part, intended to be placed facing the anterior muscle wall, the upper part of the os pubis and Cooper's ligament, and a second part called the lower part, intended to be placed facing the iliac and spermatic vessels and part of the psoas muscle, said non-porous coating being present on the second face of the textile over at least an upper region of said upper part.

Thus, as will be explained later in the detailed description, it is possible to fold the textile of the prosthesis of the invention in such a way that the fastening means do not become entangled in the textile during the passage of the prosthesis through the trocar, and in such a way that the deployment of the prosthesis is easy when it leaves the trocar. In one embodiment of the invention, said porous coating is present only on said upper region of said upper part. By virtue of the specific folding of the prosthesis as explained below, such an embodiment not only allows the prosthesis to be delivered to the implantation site by trocar without the fastening means inconveniently catching and with easy deployment of said prosthesis, but also limits the amount of foreign material, such as the material of the non-porous coating, that is introduced into the patient's body and that has to be eliminated by the patient's metabolism. Therefore, said upper region, that is to say the surface of the second face of the textile covered by the non-porous coating, preferably represents approximately two thirds of the surface of said upper part. Such embodiments make it possible to fold the prosthesis to permit passage of the prosthesis through the trocar without the fastening means catching in the textile, while at the same time minimizing the amount of foreign material, such as the non-porous coating, introduced into the human body during implantation of the prosthesis.

In one embodiment of the prosthesis according to the invention, said non-porous coating consists in a mixture of pepsin-treated collagen and glycerol. An aspect of the invention is therefore a prosthesis for repair of an inguinal hernia, which prosthesis is intended to be implanted by a posterior or open laparoscopic route and comprises:

an openworked textile made of biocompatible material, comprising a first face intended to be placed facing the biological tissues of the inguinal region, and a second face arranged opposite said first face and intended to be placed facing the peritoneum, said first face being provided with fastening means that are able to fix said textile in said biological tissues of the inguinal region, characterized in that at least a part of said second face is covered with a non-porous coating consisting in a mixture of pepsin-treated collagen and glycerol. The collagen can be oxidized or non-oxidized. Such a mixture makes it possible to obtain a non-porous coating that does not dissolve upon contact with an aqueous composition at a temperature of 20-25° C. but that does dissolve in the human body at 37° C., within a period of between 15 minutes and 4 weeks, and that is then eliminated naturally by the human metabolism.

The non-oxidized pepsin-treated collagen suitable for preparing the non-porous coating according to the invention can be prepared, for example, as follows: pigskins are ground in acid medium in order to obtain a paste, after which the dermis is precipitated in the presence of NaCl solution. The dermis is then degreased in the presence of solvents, then digested in the presence of hydrochloric acid and pepsin. After extraction of the pepsin, the product obtained is treated with sodium hydroxide (precipitation and viral deactivation) and then treated using hydrochloric acid, followed by drying in the presence of solvents.

In order to obtain a non-porous coating that takes longer to dissolve, it is possible to use oxidized pepsin-treated collagen. For example, the non-oxidized pepsin-treated collagen obtained above can be oxidized by treatment with periodic acid in the presence of hydrochloric acid. These chemical agents permit oxidation of hydroxylysine and therefore chemical cross-linking of the collagen on itself by subsequent increase in the pH of the solution of oxidized collagen.

The non-porous coating can, for example, be in the form of a film obtained by jellification of a solution containing a mixture of oxidized or non-oxidized pepsin-treated collagen and glycerol.

In one embodiment, said non-porous coating consists in a mixture of pepsin-treated collagen and glycerol and is in the form of a film, the surface density of pepsin-treated collagen ranging from 2 to 8 mg/cm$^2$, and the surface density of glycerol ranging from 0.1 to 10 mg/cm$^2$. The respective surface densities of the pepsin-treated collagen and of the glycerol in the film are calculated from the initial concentrations of these components in the solution prior to jellification.

In one embodiment, said non-porous coating consists in a mixture of non-oxidized pepsin-treated collagen and glycerol and is in the form of a film, the surface density of non-oxidized pepsin-treated collagen ranging from 2.6 to 8 mg/cm$^2$, and preferably being approximately 5 mg/cm$^2$, for example approximately 5.29 mg/cm$^2$, and the surface density of glycerol ranging from 0.1 to 10 mg/cm$^2$, and preferably being approximately 3 mg/cm$^2$, for example approximately 2.35 mg/cm$^2$. Such embodiments allow the non-porous coating to rapidly dissolve upon contact with the biological fluids at 37° C., for example within a period of between 15 minutes and 48 hours. Moreover, it has been found that a textile in which at least a part of said second face is covered with a non-porous coating of this kind provides a reduction in the catching points, during passage through a trocar, of at least 50% compared to the same textile without any coating.

In another embodiment of the prosthesis according to the invention, said non-porous coating comprises oxidized pepsin-treated collagen, optionally glycerol and optionally polyethylene glycol. Thus, in one embodiment, said non-porous coating comprises oxidized pepsin-treated collagen, optionally glycerol and optionally polyethylene glycol and is in the form of a film, the surface density of oxidized pepsin-treated collagen ranging from 2 to 7 mg/cm$^2$, and preferably being approximately 3.6 mg/cm$^2$, the surface density of glycerol ranging from 0 to 3 mg/cm$^2$, and preferably being approximately 0.72 mg/cm$^2$, the surface density of polyethylene glycol ranging from 0 to 2.5 mg/cm$^2$, and preferably being approximately 1.21 mg/cm$^2$. Like above, the respective surface densities of the oxidized pepsin-treated collagen and of the optional other components in the film are calculated from the initial concentrations of these components in the solution prior to jellification. Such an embodiment allows less rapid dissolution of the non-porous coating upon contact with the biological fluids at 37° C., for example within a period of 1 to 4 weeks. Moreover, it has been found that a textile in which at least a part of said second face is covered with a non-porous coating of this kind provides a reduction in the catching points, during passage through a trocar, of at least 50% compared to the same textile without any coating. A non-porous coating of this kind also allows adherences to be minimized.

In other embodiments of the prosthesis according to the invention, the non-porous coating comprises polyvinyl alcohol, optionally glycerol and optionally polyethylene glycol. Thus, in one embodiment, said non-porous coating comprises polyvinyl alcohol, optionally glycerol and optionally polyethylene glycol and is in the form of a film, the surface density of polyvinyl alcohol ranging from 2 to 7 mg/cm$^2$, and preferably being approximately 3.6 mg/cm$^2$, the surface density of glycerol ranging from 0 to 3 mg/cm$^2$, and preferably being approximately 0.72 mg/cm$^2$, and the surface density of polyethylene glycol ranging from 0 to 2.5 mg/cm$^2$, and preferably being approximately 1.21 mg/cm$^2$.

In one embodiment of the prosthesis according to the invention, the prosthesis is provided with a means for indicating the orientation of the prosthesis.

As has been seen above, the specific nature of the inguinal region, which is not symmetrical, means that the orientation of the prosthesis is imperative during implantation. This is because the upper part of the prosthesis often has a larger surface than the lower part. It is therefore imperative that the upper part of the prosthesis is correctly positioned facing the anterior muscle wall, the upper part of the os pubis and Cooper's ligament, and that the lower part of the prosthesis is correctly positioned facing the iliac and spermatic vessels and part of the psoas muscle. For example, said means for indicating the orientation of the prosthesis is in the form of a zone having a different colour than the rest of the prosthesis. In one embodiment of the invention, with said textile being in the form of a knit, the zone of different colour is obtained by knitting with a yarn of a different colour than the yarn or yarns used for knitting the rest of said textile. Such an embodiment therefore requires only a single knitting step in order to produce both the textile forming the prosthesis and also the means for indicating the orientation of this prosthesis. The method of production of the prosthesis is thus optimized. Moreover, since said means for indicating the orientation of the prosthesis is therefore integral with said textile, there is no risk of its detaching from the prosthesis. In particular, there is no risk of its being damaged during passage of the prosthesis through the trocar for delivering the prosthesis to the implantation site.

In one embodiment of the invention, said means for indicating the orientation of the prosthesis is situated in a medial part of the prosthesis. Within the context of the present application, "medial part" is understood as the part situated in the direction of the median plane of the human body. Thus, in the case where the means for indicating the orientation of the prosthesis according to the invention is, for example, a band with a colour different than the rest of the prosthesis, and this band is situated in the medial part of the prosthesis, the surgeon immediately knows that he has to direct this band of colour towards the os pubis when positioning the prosthesis. The surgical manoeuvre is thus made easier for him.

In one embodiment of the invention, said textile comprises a seam that at least partially delimits a border between said upper part and said lower part, said seam generally following an oblique line that starts from a starting point situated in the lower portion of a side of width 1 of said rectangle and terminates at an end point situated approximately at two thirds of the length L of the rectangle and half way along the width 1 of the rectangle. Thus, the seam can also serve as a positioning guide for the surgeon, this seam preferably having to be placed in the inguinal region at the intersection of the parietal and vascular planes to permit optimal positioning of the prosthesis. In one embodiment of the invention, said seam forms a fold of the textile, said fold causing said lower part of said textile to form naturally an angle to the plane of said upper part of said textile. Thus, the seam can give the textile a three-dimensional shape, similar to the anatomy of the inguinal region, by forming a fold in the textile, in such a way that the lower part of the textile tends naturally to form an angle with the upper part of said textile, this angle corresponding to the angle formed anatomically by the intersection of the parietal and vascular planes.

In one embodiment of the prosthesis according to the invention, said textile is a knit based on at least a first yarn of biocompatible polymer material defining said first and second faces, and at least a second yarn in the form of a biocompatible hot-melt monofilament forming said fastening means by melting of loops generated by said second yarn, the pattern chart followed for knitting said first and second yarns on a warp knitting machine with three guide bars B1, B2, B3 being the following, according to the standard ISO 11676:

Bar B1: 1.0/0.1//
Bar B2: 1.0/7.7/6.6/7.7//
Bar B3: 2.1/50.5/3.4/0.0//
said second yarn following the pattern chart of bar B3.

Such an embodiment makes it possible to optimize the formation of the openings of the textile in order to further limit the possibilities of entanglement of the fastening means in the textile.

In one embodiment of the invention, said first yarn is a monofilament yarn of polyethylene terephthalate (PET) and said second yarn is a monofilament yarn of polylactic acid (PLA). Such an embodiment makes it possible to obtain a textile that further limits the possibilities of entanglement of the fastening means in the textile, since the different monofilament yarns are less likely than multifilament yarns to catch the fastening means.

The present application also describes a method for treatment of an inguinal hernia, comprising the following steps:
  a prosthesis as described above is made available,
  said prosthesis is hydrated with an aqueous composition, for example a saline solution of 9% NaCl,
  the prosthesis is folded by first of all folding the lower part of the prosthesis onto the lower region of the upper part, with the fastening means to the outside, after which the assembly is folded onto the upper region of the upper part of the textile, onto the second face covered with the non-porous coating,
  the prosthesis, thus folded, is introduced into a trocar in order to deliver the prosthesis to the implantation site in the inguinal region,
  the prosthesis is easily deployed, the fastening means not being entangled in the textile,
  by virtue of the indicating means of the prosthesis, for example the band that has a colour different than the rest of the textile and that is situated in the medial part of the prosthesis, this medial part is oriented in the direction of the os pubis,
  the prosthesis is fitted in place facing the surrounding biological tissues, by positioning the upper part of the textile facing the anterior muscle wall, the upper part of the os pubis and Cooper's ligament, and the lower part of the textile facing the iliac and spermatic vessels and part of the psoas muscle, if appropriate with the aid of the seam, by placing the latter at the intersection of the parietal and vascular planes, the first face provided with the barbs being placed against the biological tissues of the inguinal region, and the second face, of which the non-porous coating dissolves upon contact with the biological fluids at 37° C., being placed against the peritoneum.

During the hydration of the prosthesis, before its introduction into the trocar, the non-porous coating maintains its integrity: it does not dissolve in the saline composition since the temperature does not exceed 25° C. Thus, the prosthesis can be easily folded to permit optimal passage through the trocar. Once the prosthesis has been delivered to the implantation site, with the biological fluids of the patient's body being at a temperature of close to 37° C., the non-porous coating dissolves.

By virtue of the fastening means, such as barbs, the prosthesis of the invention fixes naturally to the biological tissues of the inguinal region.

BRIEF DESCRIPTION OF THE DRAWINGS

The advantages of the present invention will become clearer from the following detailed description and example and from the attached drawings, in which:

FIGS. 8A to 8C show the pattern charts followed for knitting a textile suitable for a prosthesis according to the invention, FIGS. 9A to 9C show side views of the prosthesis of FIG. 2 during three steps for specific folding of the prosthesis.

DETAILED DESCRIPTION

Figure 2:
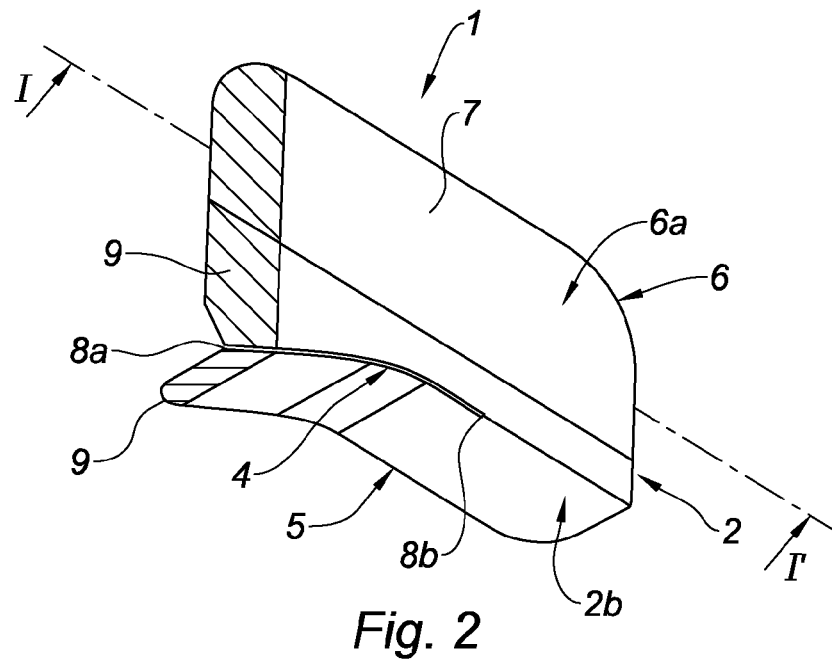
FIG. 2 is a perspective view of a prosthesis according to the invention.
Figure 3:
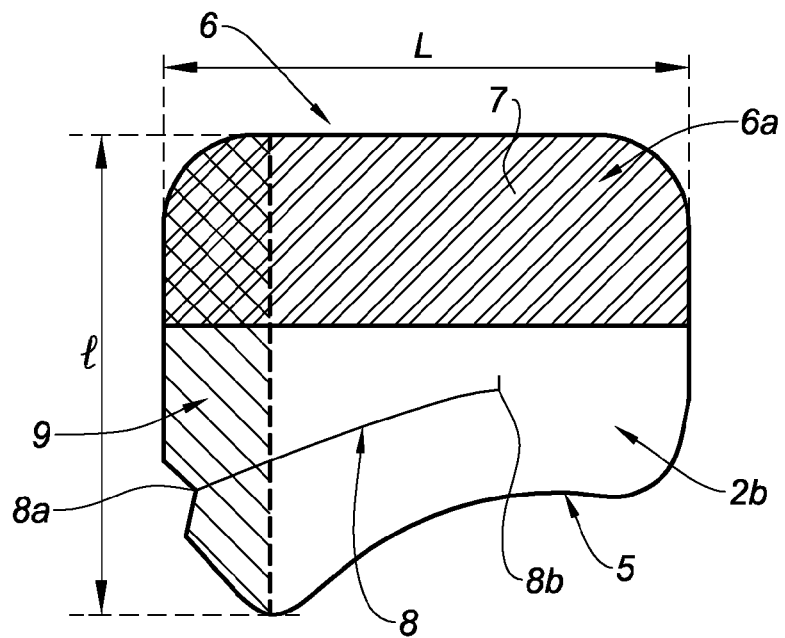
FIG. 3 is a top view of the textile used for producing the prosthesis of FIG. 2.
Figure 4:
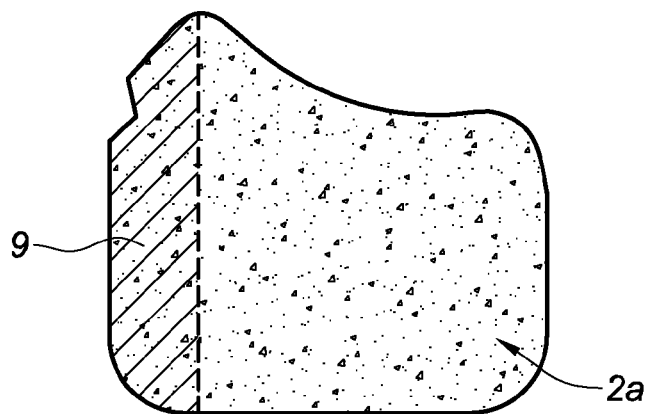
FIG. 4 is a bottom view of the textile used for producing the prosthesis of FIG. 2.

Referring to FIGS. 2 to 4, these show a prosthesis 1 according to the invention for the repair of an inguinal hernia, comprising an openworked textile 2 with two opposite faces, namely a first face 2a and a second face 2b. In FIG. 2, the prosthesis 1 has a three-dimensional shape on account of the presence of a seam 4 forming a fold in the textile 2, such that a lower part 5 of the textile 2 tends naturally to form an angle with an upper part 6 of said textile 2, this angle corresponding to the angle formed anatomically by the intersection of the parietal and vascular planes, as will be seen hereinbelow in the description. FIGS. 3 and 4 show the textile 2 in the flat state before formation of the seam 4, with its second face 2b to the top and its first face 2a to the top, respectively.

The textile 2 can be any arrangement or assembly of biocompatible yarns, fibres, filaments and/or multifilaments, obtained by knitting, weaving, braiding, or non-woven, said arrangement defining openings, cells or holes within the thickness of the textile and on the faces of the textile, these openings, cells or holes being able to form channels opening out on each side of the textile 2. Such an openworked textile 2 permits better tissue integration.

The yarns or fibres or filaments and/or multifilaments forming the arrangement of yarns constituting the textile 2 of the prosthesis according to the invention can be made of any biodegradable or non-biodegradable biocompatible material. Thus, the biodegradable materials suitable for the yarns of the textile 2 of the prosthesis 1 according to the present invention can be chosen from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers of these compounds and mixtures thereof. The non-biodegradable materials suitable for the yarns of the textile 2 of the prosthesis 1 according to the present invention can be chosen from polyethylene terephthalate (PET), polyamides, aramids, expanded polytetrafluoroethylene, polyurethane, polyvinylidene difluoride (PVDF), polybutyl esters, polyetheretherketone (PEEK), polyolefins (such as polyethylene or polypropylene), polyethers, copper alloys, silver alloys, platinum, medical grades of steel such as medical-grade stainless steel, and combinations thereof.

Figure 6:
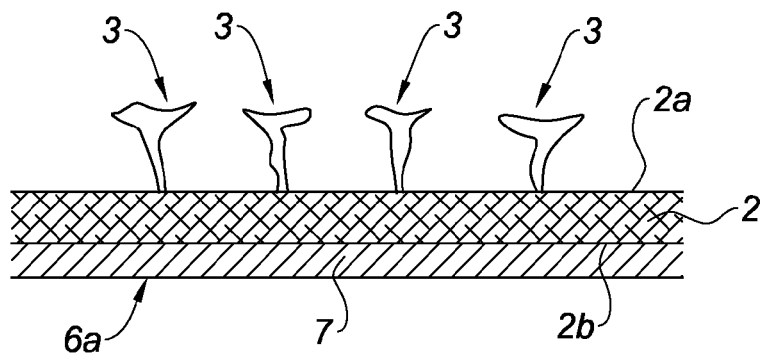
FIG. 6 is a cross-sectional view of the prosthesis of FIG. 2 in the plane I-I'.

Referring to FIGS. 4 and 6, the first face 2a of the textile 2 is provided with fastening means, represented in these figures in the form of barbs 3 jutting out from said first face 2a. These fastening means are able to fix said textile in said biological tissues of the inguinal region. These fastening means or barbs 3 can protrude from said first face 2a in a manner substantially perpendicular to the plane of said face 2a or, alternatively in an embodiment not shown, in one or more planes inclined with respect to the plane of said face.

The fastening means, for example the barbs 3, of the textile 2 of the prosthesis according to the invention can be formed from yarns, for example hot-melt monofilament yarns issuing directly from the arrangement of yarns forming the textile. Textiles and barbs of this kind, and the method of producing them, are described, for example, in the applications WO01/81667 and DE 198 32 634 or in the U.S. Pat. Nos. 6,596,002 and 5,254,133.

For example, the barbs 3 are formed from monofilament yarns made of polylactic acid.

Alternatively, the fastening means, for example the barbs, of the textile of the prosthesis according to the invention can be any kind of hook made entirely from biocompatible material and integral with the arrangement of yarns forming said textile, irrespective of whether these hooks have been incorporated in said fabric during the manufacture (braiding, knitting, weaving, etc.) of said arrangement of yarns or have been attached later.

Preferably, as is shown in FIG. 6, the fastening means are barbs 3 in the shape of a stalk topped by a head; the average size of the heads of the barbs varies in general from 300 μm to 500 μm.

Textiles with barbs suitable for the present invention are described in WO01/81667, for example, or are also commercially available from the company Sofradim Production under the trade name Parietex® Progrip or Parietene® Progrip.

In one embodiment, the textile 2 is a knit based on at least a first yarn of biocompatible polymer material defining said first and second faces (2a, 2b) and at least a second biocompatible hot-melt monofilament yarn forming said fastening means by melting of loops generated by said second yarn, the pattern chart followed for knitting said first and second yarns on a warp knitting machine with three guide bars B1, B2, B3 being the following, according to the standard ISO 11676:

Bar B1: 1.0/0.1//
Bar B2: 1.0/7.7/6.6/7.7//
Bar B3: 2.1/50.5/3.4/0.0// said second yarn following the pattern chart of bar B3.

The above pattern chart is illustrated in FIGS. 8A to 8C for bar B1, bar B2 and bar B3, respectively, in a representation well known to a persn skilled in the art. A pattern chart of this kind, followed for knitting the yarns of the knit, generates a particular structure of the textile 2, that is to say a specific arrangement between the different openings in the faces of the textile 2, the respective size of these different openings and the disposition and distribution of the barbs 3 being such that, even if some of the barbs 3 present on the first face 2a come to be trapped within some of the openings present on the second face 2b when the prosthesis is rolled up on itself under the effect of an external stress, for example the stresses exerted by the surgeon when folding the prosthesis in order to introduce it into a trocar, then the stress exerted by the inner walls of the trocar, a large number of the trapped barbs 3 will be freed automatically or under the effect of a very weak unrolling force when said stress is relaxed.

Moreover, and also preferably, said first yarn is a monofilament yarn of polyethylene terephthalate (PET) and said second yarn is a monofilament yarn of polylactic acid (PLA).

The first yarn(s) of the knit according to the invention are those that follow the pattern charts for bars B1 and B2. They constitute the foundation or base of the knit of the prosthesis 1 according to the invention, since the second yarn, namely a hot-melt monofilament yarn, which generates the barbs 3, is regularly cut in the area of the loops that it forms. The generation of barbs from loops of hot-melt yarn is known and is described, for example, in the document WO01/81667. When the first yarn(s) are monofilament yarns, the possible presence of asperities or of points of fastening of the barbs is limited, and the force needed to unroll the knit after the prosthesis has been rolled up as described above is very low.

The textile 2 of the prosthesis according to the invention can have a thickness, including the length of the barbs 3, of from 1 to 2 mm, for example approximately 1.4 mm.

Referring to FIG. 3, in which the textile 2 is shown when flat and before production of the seam 4 which gives the prosthesis 1 its three-dimensional character, the second face 2b of the textile 2 is partially covered with a non-porous coating 7 consisting in a material that is hydrosoluble at 37° C. and non-hydrosoluble at 25° C.

For example, said non-porous coating consists in a mixture of pepsin-treated collagen and glycerol.

In one embodiment, said non-porous coating consists in a mixture of pepsin-treated collagen and glycerol and is in the form of a film, the surface density of pepsin-treated collagen ranging from 2 to 8 mg/cm$^2$, and the surface density of glycerol ranging from 0.1 to 10 mg/cm$^2$.

For example, said non-porous coating consists in a mixture of non-oxidized pepsin-treated collagen and glycerol and is in the form of a film, the surface density of non-oxidized pepsin-treated collagen ranging from 2.6 to 8 mg/cm$^2$, and preferably being about 5.29 mg/cm$^2$, and the surface density of glycerol ranging from 0.1 to 10 mg/cm$^2$, and preferably being approximately 2.35 mg/cm$^2$. Such an embodiment allows the non-porous coating to rapidly dissolve on contact with the biological fluids at 37° C., for example between 15 minutes and 48 hours. Moreover, it has been found that a textile in which at least part of said second face is covered with a non-porous coating of this kind provides a reduction in the catching points, during passage through a trocar, of at least 50% compared to the same textile without any coating.

In another embodiment of the prosthesis according to the invention, said non-porous coating comprises oxidized pepsin-treated collagen, optionally glycerol, and optionally polyethylene glycol. Thus, in one embodiment, said non-porous coating comprises oxidized pepsin-treated collagen, optionally glycerol and optionally polyethylene glycol and is in the form of a film, the surface density of oxidized pepsin-treated collagen ranging from 2 to 7 mg/cm$^2$, and preferably being approximately 3.6 mg/cm$^2$, the surface density of glycerol ranging from 0 to 3 mg/cm$^2$, and preferably being approximately 0.72 mg/cm$^2$, the surface density of polyethylene glycol ranging from 0 to 2.5 mg/cm$^2$, and preferably being approximately 1.21 mg/cm$^2$. Such an embodiment allows less rapid dissolution of the non-porous coating on contact with the biological fluids at 37° C., for example from 1 to 4 weeks. Moreover, it has been found that a textile in which at least part of said second face is covered with a non-porous coating of this kind provides a reduction in the catching points, during passage through a trocar, of at least 50% compared to the same textile without any coating. A non-porous coating of this kind also allows adherences to be minimized.

In other embodiments of the prosthesis according to the invention, the non-porous coating comprises polyvinyl alcohol, optionally glycerol, and optionally polyethylene glycol. Thus, in one embodiment, said non-porous coating comprises polyvinyl alcohol, optionally glycerol and optionally polyethylene glycol and is in the form of a film, the surface density of polyvinyl alcohol ranging from 2 to 7 mg/cm$^2$, and preferably being approximately 3.6 mg/cm$^2$, the surface density of glycerol ranging from 0 to 3 mg/cm$^2$, and preferably being approximately 0.72 mg/cm$^2$, and the surface density of polyethylene glycol ranging from 0 to 2.5 mg/cm$^2$, and preferably being approximately 1.21 mg/cm$^2$.

Figure 7:
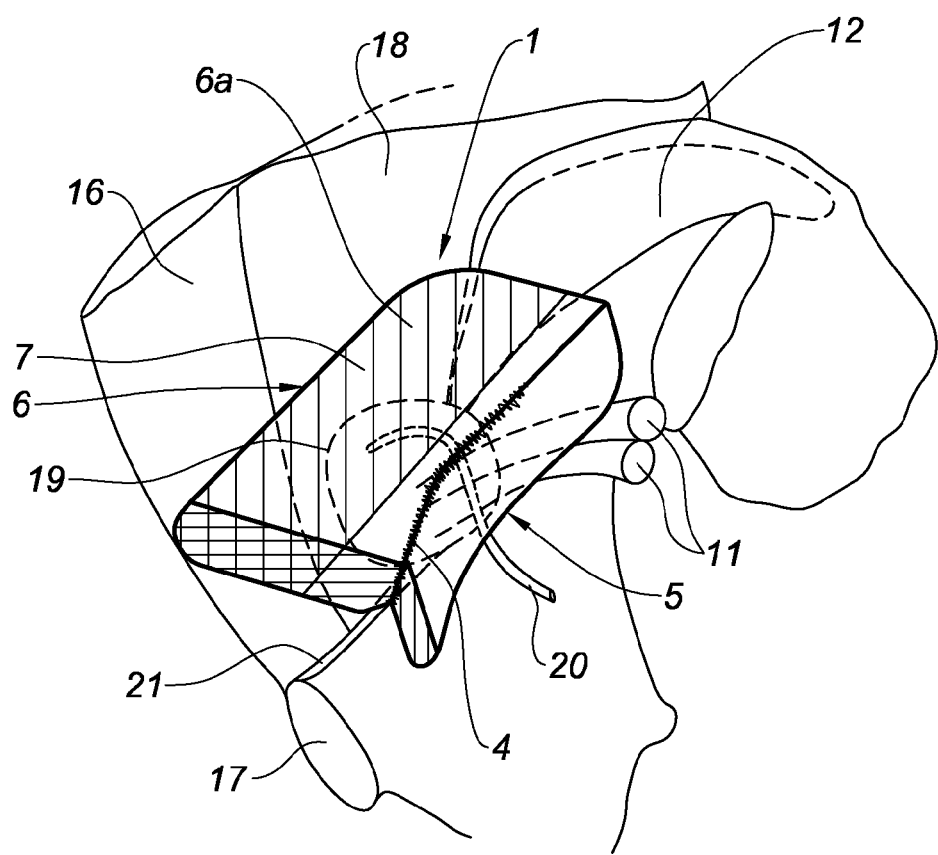
FIG. 7 is a perspective view of the prosthesis of FIG. 2 once implanted and positioned with respect to the anatomical elements of the extraperitoneal inguinal region, on the right-hand side of a human body, seen from the inside outwards, that is to say towards the outside of the body.

Referring to FIGS. 2, 3 and 7, the textile 2 when flat has the overall shape of a rectangle with length L and width l (see FIG. 3), the textile 2 determining in the direction of its width l a first part called the upper part 6, intended to be placed facing the anterior muscle wall (16, 18), the upper part of the os pubis 17 and Cooper's ligament 21, and a second part called the lower part 5, intended to be placed facing the iliac vessels 11 and spermatic vessels 20 and part of the psoas muscle. By way of example, L can be of the order of 15 cm and l can be of the order of 13 cm. Referring to FIG. 3, the upper part 6 of the textile 2 is separated at least partially from the lower part 5 by a line 8 indicating the place where the seam 4 of the prosthesis 1 of FIG. 1 will be made.

As will be seen from these figures and from FIG. 3, the non-porous coating is in the form of a film 7 which is present on an upper region 6a of the upper part 6 of the textile 2. This upper region 6a represents approximately two thirds of the surface of the upper part 6 of the textile 2. In particular, the non-porous coating 7 is present only on this upper region 6a of the upper part 6 of the textile 2. The advantage of such an embodiment will become clear later in the description.

Figure 5:
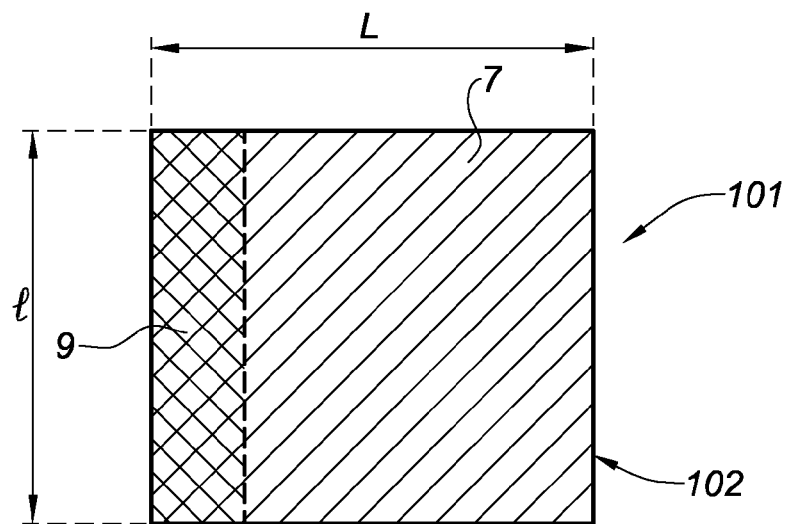
FIG. 5 is a top view of the textile used for producing a variant of the prosthesis according to the invention.

In another embodiment of the prosthesis according to the invention, shown in FIG. 5, the prosthesis 101, and therefore the textile 102, has the shape of a rectangle. In the example shown, the non-porous coating 7 is present on the whole of the second face of the textile 102.

Referring to FIGS. 2-4, the prosthesis 1 is also provided with a means for indicating the orientation of the prosthesis, said indicating means being in the form of a band 9 having a colour different than the colour of the rest of the prosthesis 1, this band of colour 9 being situated in the medial part of the prosthesis 1. The "medial part" of the prosthesis is understood as the part of the prosthesis that will be situated in the direction of the median plane of the human body once the prosthesis has been implanted. When the textile 2 is a knit, as has been described above, the band 9 of different colour is obtained by knitting with a yarn of a different colour than the yarn or yarns used for knitting the rest of the textile 2.

Referring to FIGS. 2 and 3, the textile 2 comprises a seam 4 that at least partially delimits a border between said upper part 6 and said lower part 5, said seam 4 generally following an oblique line 8 (see FIG. 3) that starts from a starting point 8a situated in the lower portion of a side of width l of said rectangle and terminates at an end point 8b situated at approximately two thirds of the length L of the rectangle and half way along the width l of the rectangle. Moreover, the seam 4 forms a fold of the textile 2, said fold causing said lower part 5 of the textile 2 to form naturally an angle to the plane of the upper part of said textile 2, as is shown in FIG. 2. As will become clear from the description below, this angle preferably corresponds to the angle formed anatomically by the intersection of the parietal and vascular planes in the inguinal region, as has been described for FIG. 1.

Thus, by virtue of the presence of the seam 4, as will be seen from FIGS. 3 and 7, the upper part 6 is substantially planar, whereas the lower part 5 of the textile 2 of the prosthesis 1 has an undulated and anatomical developed shape for matching the general shape of the lower inguinal structures, especially the spermatic and iliac vessels and the psoas muscle, as will be seen from FIG. 7. The oblique line 8 followed by the seam 4 gives the latter a curved shape, the lower part 5 thus forming with the upper part 6 an angle corresponding to the angle formed by the parietal and vascular planes at the intersection thereof in the inguinal region of a human body. Thus, the upper part 6 and the lower part 5 are asymmetrical, which means that a left-hand prosthesis or right-hand prosthesis will be used depending on which side the hernia to be treated is located. As is shown in FIG. 7, the prosthesis of FIG. 2 is a prosthesis for the repair of an inguinal hernia on the right-hand side of a patient. A prosthesis suitable for the repair of an inguinal hernia on the left-hand side of a patient would have a shape the mirror image of the prosthesis 1 of FIG. 2.

Preferably, the upper part 6 can have a height of up to approximately 15 cm, and the lower part 5 can have a depth of between approximately 2 cm and approximately 6 cm.

A prosthesis of this kind ensures that all of the anatomical elements described above are covered, without leaving empty spaces that could possibly cause a recurrence. In particular, the region around the iliac and spermatic vessels is particularly well protected. This therefore avoids one of the main causes of secondary hernias, which can be even more difficult to treat on account of the deterioration of the anatomical structures that has been caused by the earlier hernia.

The prosthesis according to the invention, in particular the prosthesis 1 of FIGS. 2-4, can be produced as follows:

- an openworked textile of biocompatible material is made available, such as the textile 2 in the figures, comprising a first face 2a provided with fastening means, such as barbs 3, that are able to fix said textile in biological tissues of the inguinal region, for example as described above, and a second face: the textile 2 can be a knit obtained in the shape of a rectangle, with the band of different colour already present, obtained by knitting, as described in Example 1 below;
- a rectangular shape as shown in FIG. 5 or an anatomical shape as shown in FIG. 3 is cut from this rectangle, delimiting an upper part 6 and a lower part 5 of the textile 2;
- if appropriate, the seam 4 is made along the line 8 (FIG. 3) by forming a fold in order to give the prosthesis a three-dimensional shape. The seam 4 is terminated at an end point 8a, as is described below. This three-dimensional shape ensures that the inguinal space is well covered;
- at least a part of said second face is covered with a non-porous coating composed of a material that is hydrosoluble at 37° C. and non-hydrosoluble at 25° C.; the preparations of the composition of the non-porous coating and its application to the second face of the textile 2 is described in more detail in Example 1 below.

The use and the implantation of the prosthesis according to the invention will now be described with reference to the treatment of an inguinal hernia on the right-hand side of a patient by a posterior laparoscopic approach using the prosthesis 1 from FIGS. 2-4.

The technique used in the laparoscopic intervention, for example, is well known to a person skilled in the art and, consequently, will not be described in detail. In this technique, one or more trocars are introduced into the extraperitoneal space, that is to say posterior to the rectus abdominis muscle and the fascia *transversalis*, the extraperitoneal working space being created by insufflation and separation of the peritoneum and the abdominal wall.

Figure 1:
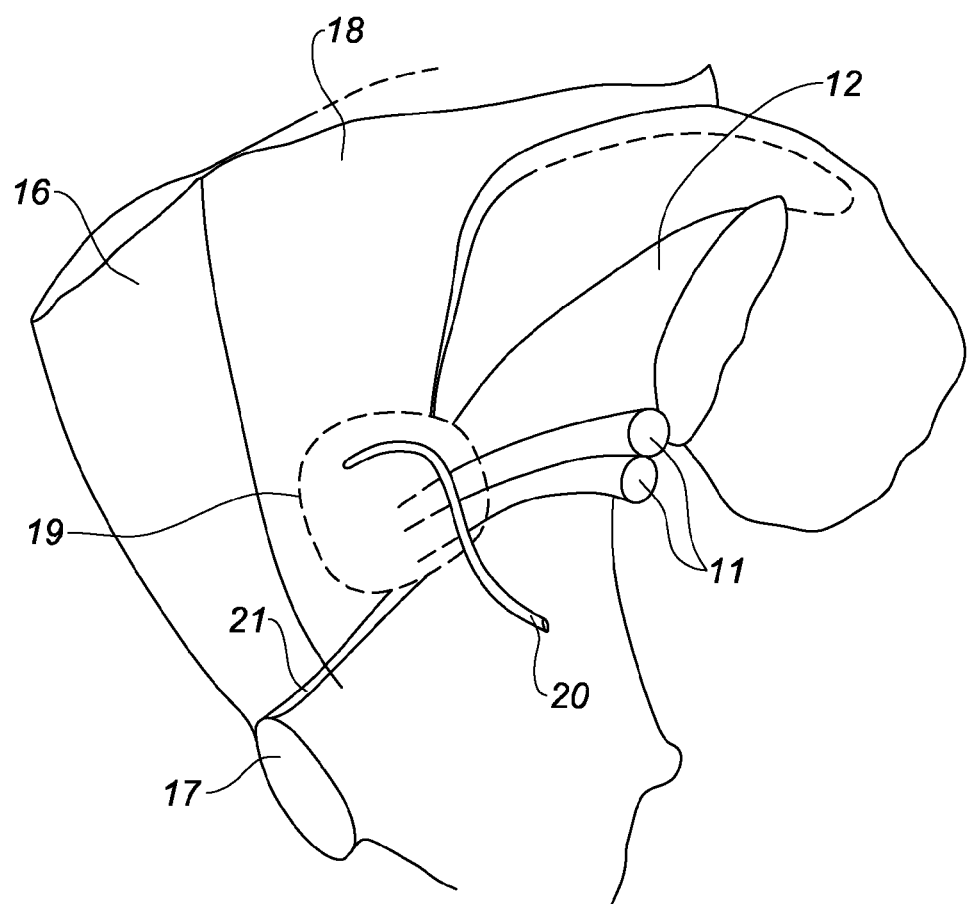
FIG. 1 is a perspective view of the inguinal region on the right-hand side of a human body.

The perspective views in FIGS. 1 and 7 show, on the one hand, the anatomical elements of the extraperitoneal inguinal region on the right-hand side of a human body, seen from the inside outwards, that is to say towards the outside of the body as has been described above, and, on the other hand, a view of the positioning of the prosthesis according to the present invention in relation to these elements once it has been implanted.

It can be clearly seen in FIG. 1 that the inguinal region is particular in that the elements described above are not all in the same spatial plane, but instead are arranged in an oblique arrangement from the top downwards and from the outside inwards. In the case of an inguinal hernia, the prosthesis implanted after reduction of the hernia must ensure satisfactory covering by adapting to the contours of the region and by respecting the obliqueness of the inguinal space.

To proceed with the intervention, the surgeon takes hold of the prosthesis 1 from FIG. 2 and hydrates this prosthesis 1 with an aqueous composition, for example a 9% NaCl saline solution. During the hydration of the prosthesis 1, before its introduction into the trocar intended to deliver it to the inguinal space, the non-porous coating 7 maintains its integrity: it does not dissolve in the saline composition since the temperature does not exceed 25° C. Thus, the prosthesis 1 can be easily folded, in particular specifically folded to permit optimal passage through the trocar and easy deployment of the prosthesis 1, as is described hereinbelow.

The folding of the prosthesis 1 from FIG. 2 is described hereinbelow with reference to FIGS. 9A to 9C. FIG. 9A shows a side view of the prosthesis 1 from FIG. 2 in its deployed configuration. The surgeon begins folding the prosthesis 1 by first of all folding the lower part 5 of the prosthesis 1 onto the lower region of the upper part 6 free of non-porous coating, with the fastening means, in other words the barbs 3, to the outside, as is shown in FIG. 9B; this first folding is performed along the seam line 4: these two parts are folded one onto the other, second face 2b on second face 2b, such that the barbs 3 cannot become entangled in the openings of the textile 2.

Referring to FIG. 9C, the surgeon then folds the assembly made up of "lower part 5+lower region of the upper part 6" onto the upper region 6a of the upper part 6 of the textile 2, onto the second face 2b covered with the non-porous coating 7. Thus, the barbs 3 of the lower part 5 are brought into contact with the non-porous coating 7, and not with the openings of the textile 2. By virtue of the pliability of the prosthesis 1, in particular of the textile 2, reinforced by the prior hydration of the prosthesis 1 as has been described above, this folding is easy to do, as is also the subsequent step of introducing the roll thereby obtained into a trocar (not shown), for example with an internal diameter of 10 mm.

As will be clear from the description of this folding, the presence of the non-porous coating 7 on only approximately two thirds of the surface of the upper part 6 of the textile 2 corresponds to an advantageous embodiment of the prosthesis 1 according to the invention. This is because this embodiment not only makes it possible to deliver the prosthesis 1 to the implantation site by trocar, without entanglement of the barbs 3 and with easy deployment of said prosthesis 1 as will be described hereinbelow, but also makes it possible to limit the amount of material constituting a foreign body, such as the material of the non-porous coating 7, that is introduced into the patient's body and that has to be eliminated by the patient's metabolism.

The surgeon then introduces the folded prosthesis 1 into the trocar in order to deliver the prosthesis to the implantation site in the inguinal region. Despite the stress exerted by the walls of the trocar, the barbs 3 do not become entangled in the openings of the textile 2 by virtue of the presence of the non-porous coating 7 which forms a barrier and does not dissolve.

Once it is at the implantation site, namely in the inguinal region as described with reference to FIG. 1, the prosthesis 1 is easily deployed by the surgeon, and the barbs 3 do not become entangled in the textile 2. Since the biological fluids of the patient's body are at a temperature close to 37° C., the non-porous coating 7 dissolves and is eliminated naturally by the patient.

By virtue of the band 9 that has a colour different than the colour of the rest of the prosthesis 1, and that is situated in the medial part of the prosthesis 1, the surgeon easily orients this medial part in the direction of the os pubis 17 (FIG. 7).

The surgeon fits the prosthesis 1 in place facing the surrounding biological tissues, by positioning the upper part 6 of the textile 2 facing the anterior muscle wall, the upper part of the os pubis 17 and Cooper's ligament 21, and the lower part 5 of the textile facing the iliac and spermatic vessels 11 and part of the psoas muscle, if appropriate with the aid of the seam 4, for example by placing the latter at the intersection of the parietal and vascular planes, the first face 2a provided with the barbs 3 being placed against the biological tissues of the inguinal region, and the second face 2b, of which the non-porous coating 7 dissolves on contact with the biological fluids at 37° C., being placed against the peritoneum (not shown).

By virtue of the barbs 3, the prosthesis 1 fixes naturally to the biological tissues of the inguinal region, and an additional step of fixing with staples or sutures is not necessary.

When the prosthesis 1 is implanted (reference may usefully be made to FIG. 7), the upper part 6 rests on the anterior muscle wall (especially the rectus abdominis muscle 16 and transverse muscle 18), the upper end of the os pubis and part of Cooper's ligament 21. The lower part 5 conforms almost completely, without leaving any appreciable spaces, to the iliac and spermatic vessels 11 and the psoas muscle 12, and the seam 4 is placed at the intersection of the parietal and vascular planes. The ductus deferens 20 is also covered and therefore protected.

The prosthesis 1 according to the invention remains in place by itself, particularly on account of its three-dimensional shape, since the seam 4 takes up a position at the intersection of the parietal and vascular planes. This allows the prosthesis 1 to follow the changes in the relative position of the various anatomical elements of the inguinal region, which changes result from the normal movement of the abdominal muscles of the subject, but without its moving away from the implantation region.

EXAMPLE 1

A prosthesis according to the invention is produced as follows:

1) Preparation of a Textile in the Form of a Knit in which the Means for Indicating the Orientation of the Prosthesis is Incorporated During Knitting On a warp knitting machine with three guide bars B1, B2, B3, a knit was produced having the following pattern chart according to the standard ISO 11676:

Bar B1: 1.0/0.1//
Bar B2: 1.0/7.7/6.6/7.7//
Bar B3: 2.1/5.5/3.4/0.0//

These pattern charts are illustrated in FIGS. 8A to 8C in a representation known to a person skilled in the art: the pattern chart for bar B1 is illustrated in FIG. 8A, the pattern chart for bar B2 is illustrated in FIG. 8B, and the pattern chart for bar B3 is illustrated in FIG. 8C.

Bar B1 and bar B2 are each threaded 1 full, 1 empty, with a monofilament yarn of polyethylene terephthalate (PET) of diameter 0.09 mm; bar B3 is threaded 1 full, 3 empty, with a thermoplastic monofilament yarn of polylactic acid of diameter 0.15 mm.

The pattern chart for bar B3 causes the thermoplastic monofilament yarn of polylactic acid to form loops. These loops are then melted, as is described in WO01/81667, in order to form barbs protruding from the first face of the textile, each loop giving rise to two barbs. The barbs that are obtained generally have the shape of a stalk topped by a head, as is shown in FIG. 6: the average size of the heads of the barbs generally varies from 300 μm to 500 μm.

The knit obtained has a thickness, including the length of the barbs, of approximately 1.4 mm.

The pattern chart followed for knitting the yarns of the knit of the present example generates a particular structure of the textile, that is to say a specific arrangement between the different openings in the faces of the textile, the respective size of these different openings and the disposition and distribution of the barbs being such that, even if some of the barbs present on the first face are trapped within some of the openings present on the second face when the prosthesis is rolled up on itself under the effect of an external stress, for example the stresses exerted by the surgeon when folding the prosthesis in order to introduce it into a trocar, then the stress exerted by the inner walls of the trocar, a large number of the trapped barbs will be freed automatically or under the effect of a very weak unrolling force when said stress is relaxed. This effect is reinforced by the fact that the yarns used are monofilament yarns.

In order that the means for indicating the orientation of the prosthesis is incorporated during the above knitting phase, bars B1 and B2 are threaded over a certain distance with PET monofilament yarns of a first colour, for example white, then over a defined second distance with PET monofilament yarns of another colour, for example green, and this is repeated over the entire width of the knitting machine.

Figure 10:
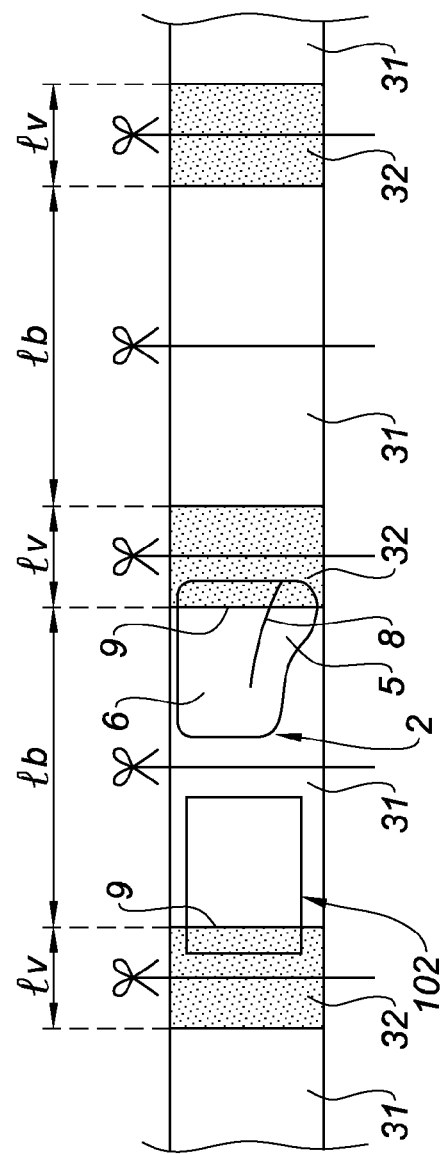
FIG. 10 is a partial top view of a knit suitable for the prosthesis according to the invention and comprising a means for indicating the orientation of the prosthesis.

This results, for example, in a succession of white bands and green bands. For example, the white bands 31 have a width Ib of 31 cm, and the green bands 32 have a width Iv of 9 cm, as is shown in FIG. 10. It then suffices to cut each white band 31 at its middle and each green band 32 at its middle, as is shown in FIG. 10, in order to obtain knits of rectangular shape with a total length of 20 cm and with a band of different colour in the region of one of the small sides of the rectangle.

Again with reference to FIG. 10, it is possible, in each rectangular knit thus obtained, to cut out either a rectangular textile 102 comprising a colour band 9 with a view to producing a prosthesis 101 according to the invention as shown in FIG. 5, or a textile 2 comprising a colour band 9, an upper part 6 and a lower part 5 and also an oblique line 8, with a view to producing a prosthesis according to FIG. 2. In the latter case, a seam is formed along the line 8 by forming a fold in order to obtain a three-dimensional textile, as has been explained in the present application with reference to FIG. 2.

2) Preparation of the Composition Intended to Form the Coating of Non-Porous Material Particles of non-oxidized pepsin-treated collagen are prepared by grinding pigskins in acid medium in order to obtain a paste, after which the dermis is precipitated in the presence of NaCl solution. The dermis is then degreased in the presence of solvents, then digested in the presence of hydrochloric acid and pepsin. After extraction of the pepsin, the product obtained is treated with sodium hydroxide (precipitation and viral deactivation) and then treated using hydrochloric acid, followed by drying in the presence of solvents.

The particles of pepsin-treated collagen are then mixed with stirring at 40° C. in a solution of glycerol in water: the pH of the composition obtained is adjusted to 7.0 using a solution of sodium hydroxide (NaOH).

The composition is then heated at 60° C. with stirring, then filtered. The temperature is then brought back to 40° C., and the pH is adjusted between 4.5 and 7.0 with either a base (NaOH) or an acid (HCl), if necessary.

The concentration of the composition is adjusted to 5.4% (w/w) for the collagen and to 2.4% (w/w) for the glycerol.

The composition is maintained at 40° C.

3) Application of the Composition Obtained Under 2) to a Textile Obtained Under 1), in the Form of a Film The composition obtained under 2) is deposited on the second face 2b of the textile (2; 102):
- either over the whole surface of the second face 2b in the case of the textile 102 of the prosthesis 101 of FIG. 5,
- or only in the upper region 6a of the upper part 6 of the textile 2 in the case of the prosthesis 1 of FIGS. 2 and 3.

The composition is applied with a density of 0.092 ml/cm$^2$. It forms a gel in approximately 45 minutes.

The assembly "textile+gelled composition" is then dried in air for 12 hours until a film is obtained.

In the film, the surface density of pepsin-treated collagen is approximately 5 mg/cm$^2$, and the surface density of glycerol is approximately 3 mg/cm$^2$.

This film is non-hydrosoluble at a temperature of 20 to 25° C. and is hydrosoluble at a temperature of approximately 37° C. It dissolves in the biological fluids in approximately 15 minutes.

Prostheses according to the invention are thus obtained, for example a prosthesis 101 according to FIG. 5, or a prosthesis 1 according to FIG. 2, and these prostheses, after hydration at 20-25° C., can be folded, introduced into a trocar and then easily deployed, as described in the present application.

The invention claimed is:

1. A method for producing a prosthesis, comprising:
   providing an openworked textile of biocompatible material comprising a first face, provided with fastening means that are able to fix said textile in biological tissues of an inguinal region, and a second face,
   heating a composition including particles of pepsin-treated non-oxidized collagen and glycerol to 60° C., maintaining the composition at 40° C. following heating, covering at least a part of said second face with the composition to form a non-porous coating that is hydrosoluble at 37° C. and non-hydrosoluble at 25° C.

2. The method according to claim 1, wherein covering at least a part of said second face comprises covering a whole of said second face of said openworked textile with the non-porous coating.

3. The method according to claim 1, wherein said openworked textile further comprises an overall shape of a rectangle with a length and a width, and said openworked textile determines in the width direction a first upper part, intended to be placed facing an anterior muscle wall, an upper part of an os pubis and Cooper's ligament, and a second lower part, intended to be placed facing an iliac and spermatic vessels and part of a psoas muscle, and wherein covering at least a part of said second face comprises covering at least an upper region of said first upper part of said second face of said openworked textile with the non-porous coating.

4. The method according to claim 3, wherein covering at least a part of said second face comprises covering only said upper region of said upper part with the non-porous coating.

5. The method according to claim 4, wherein said upper region represents approximately two thirds of a surface of said upper part.

6. The method according to claim 3, further comprising forming a seam on said textile, said seam at least partially delimiting a border between said upper part and said lower part, said seam generally following an oblique line that starts from a starting point situated in a lower portion of a side of the width of said rectangle and terminates at an end point situated approximately at two thirds of the length of the rectangle and half way along the width of the rectangle.

7. The method according to claim 6, further comprising folding said textile along said seam to form a fold, said fold causing said lower part of said textile to form naturally an angle to a plane of said upper part of said textile.

8. The method according to claim 1, wherein said non-porous coating comprises a film comprising a surface density of pepsin-treated collagen ranging from 2 to 8 mg/cm$^2$ and a surface density of glycerol ranging from 0.1 to 10 mg/cm$^2$.

9. The method according to claim 1, wherein said non-porous coating comprises a film comprising a surface density of non-oxidized pepsin-treated collagen ranging from 2.6 to 8 mg/cm$^2$ and a surface density of glycerol ranging from 0.1 to 10 mg/cm$^2$.

10. The method according to claim 1, further comprising providing a means for indicating the orientation of the prosthesis to the prosthesis.

11. The method according to claim 10, wherein said means for indicating the orientation of the prosthesis is a zone having a different color than the rest of the prosthesis.

12. The method according to claim 11, wherein providing a means for indicating the orientation of the prosthesis comprises knitting with a yarn of a different color than a yarn used for knitting said textile obtaining the zone having a different color.

13. The method according to claim 11, wherein said zone having a different color of the prosthesis is situated in a medial part of the prosthesis.

14. The method according to claim 1, wherein providing an openworked textile comprises knitting at least a first yarn of biocompatible polymer material to define said first and second faces, and at least a second yarn in the form of a biocompatible hot-melt monofilament to form said fastening means by melting of loops generated by said knitting said second yarn, wherein said first and second yarns are knit on a warp knitting machine with three guide bars B1, B2, B3, according to standard ISO 11676 and the following pattern chart:

Bar B1: 1.0/0.1//
Bar B2: 1.0/7.7/6.6/7.7//
Bar B3: 2.1/5.5/3.4/0.0//
said second yarn following the pattern chart of bar B3.

15. The method according to claim 14, wherein said first yarn is a monofilament yarn of polyethylene terephthalate (PET) and said second yarn is a monofilament yarn of polylactic acid (PLA).

16. A method for producing a prosthesis, comprising:
providing an openworked textile of biocompatible material comprising a first face and a second face opposite said first face, said first face provided with fastening means that are able to fix said textile in biological tissues of an inguinal region, said textile determining in a width direction a first upper part and second lower part, and said textile in a length direction determining a zone of different color situated only in a medial part of said textile, said zone of different color including a yarn of a different color than a yarn used for forming said textile,
covering only said first upper part of said second face of said textile with a non-porous coating comprising a material that is hydrosoluble at 37° C. and non-hydrosoluble at 25° C., wherein said non-porous coating comprises a mixture of non-oxidized collagen and glycerol and said non-porous coating and said zone of different color overlap on an upper medial part of said textile.

17. The method of claim 16, wherein the non-oxidized collagen includes particles of pepsin-treated non-oxidized collagen.

* * * * *